United States Patent [19]

Kolb

[11] 4,296,638
[45] Oct. 27, 1981

[54] SAMPLING MOLTEN METAL

[75] Inventor: Gustav Kolb, Im Ohl 52, 5870 Hemer, Fed. Rep. of Germany

[73] Assignees: Mannesmann Aktiengesellschaft, Duesseldorf; Gustav Kolb, Hemer, both of Fed. Rep. of Germany

[21] Appl. No.: 92,849

[22] Filed: Nov. 9, 1979

[30] Foreign Application Priority Data

Nov. 11, 1978 [DE] Fed. Rep. of Germany ....... 2849333

[51] Int. Cl.³ .............................................. G01N 1/12
[52] U.S. Cl. ................................ 73/863.21; 73/864.57
[58] Field of Search ..................... 73/425.4 R, DIG. 9

[56] References Cited

U.S. PATENT DOCUMENTS 3,974,698  8/1976  Scott ............................. 73/DIG. 9
4,116,070  9/1978  Falk ..................................... 73/425.4
4,148,221  4/1979  Bardenhever ...................... 73/425.4

Primary Examiner—S. Clement Swisher
Attorney, Agent, or Firm—Smyth, Pavitt, Siegemund & Martella

[57] ABSTRACT

A ceramic body includes a disk-shaped mold cavity in its upper part and a slag retention chamber underneath; these chambers are interconnected by a duct extending downward from the bottom of the mold and being continued by a ceramic tube traversing centrally the retention chamber and ending near the bottom thereof. A reversal chamber is excentrically disposed under this tube end, and diametrally thereto ends the feed duct.

6 Claims, 2 Drawing Figures

SAMPLING MOLTEN METAL

BACKGROUND OF THE INVENTION

The present invention relates to a device for sampling molten metal, e.g., steel. The German printed patent application No. 28,40,745.6 (see also U.S. Pat. No. application 076,450 filed Sept. 17, 1979) describes a device of the type to which the invention pertains. In particular, a device is described therein which includes a ceramic body being provided with a slag-retaining chamber. A duct extends alongside that chamber for connecting it with the sample chamber which is constructed as a flat, cylindrical mold. This device operates quite satisfactorily, but the amount of slag which can be captured is somewhat limited in relation to the overall dimensions (cross section) of the cylindrically shaped ceramic body.

DESCRIPTION OF THE INVENTION

It is an object of the present invention to provide a new and improved device for sampling molten metal, e.g., steel, wherein the improvement is particularly directed towards increasing the dimensions of the slag retention chamber. A large chamber for that purpose was found to be of significant advantage because the sample proper should be slag free.

In accordance with the preferred embodiment of the present invention, it is suggested to provide a slag retention chamber underneath the mold chamber and to interconnect these chambers by a duct, a portion of which is a refractory tube having an entrance near the bottom of the slag retention chamber. The tube is loosely affixed to a portion of the body, and continues a duct in a portion of the ceramic body which duct runs downward from the bottom of the mold chamber. The upper part of the tube is preferably sealed against the duct wall.

An inlet and feed duct ends in the slag retention chamber, preferably in a level above the lower end of the tube. The lower portion of the slag retention chamber includes a flow-reversing chamber portion extending below the entrance level of the tube. This tube is preferably held, additionally, right at its lower end, adjacent to the entrance of the tube for the slag-free steel. The slag retention chamber has preferably an uneven wall to enhance the slag retention capability; the slag will readily adhere to the wall.

Figure 1:
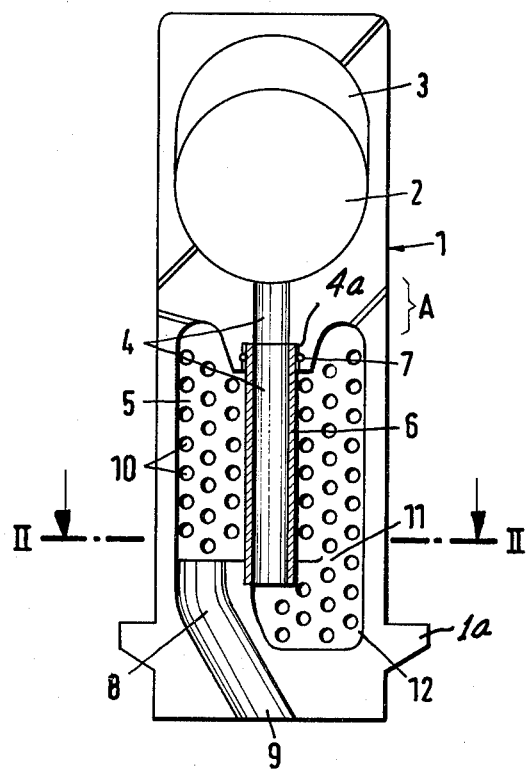
FIG. 1 is a cross section through the new and improved sampling device in accordance with the preferred embodiment and best mode of the present invention.

Proceeding now to the detailed description of the drawings, the figures show a ceramic body 1 of cylindrical construction. The body is actually composed of two parts; or one can say, the body is longitudinally partitioned. The plane of FIG. 1 is actually that partioning plane 1, and the view is directed towards the in face surface of one-half of the body. This two-part body is stuck into a cardboard tube (not shown) whose front end bears against an annular shoulder 1a. The sampling body 1 is shown in FIG. 1 in the operating position.

The upper part of body 1 contains a sampling chamber 2 which can also be regarded as a mold whose contour has the negative configuration of the sample to be taken. Chamber 2 is of (negative) disk-shaped configuration, except that the upper part is extended into a crescent-shaped chamber portion 3. Chamber 2 is a flat upright cylinder, and the crescent extension 3 is thinner in the direction transverse to the plane of the drawing. Upon fitting the mold chamber with metal and following solidification thereof, the sample is a small disk with a lamella on one side.

The bottom of chamber 2 is connected to a short, upright duct 4 whose lower end 4a is of a wider diameter, and a tube 6 has been loosely inserted to serve as a continuation of that duct. Tube 6 is made of ceramic or quartz and traverses concentrically a rather large slag capture and retention chamber 5. The lower end of tube 6 is held on a three-quarter ledge in the bottom portion of chamber 5.

In order to seal the gap between tube 6 and widened portion 4a of duct 4, a wire 7 is looped around the tube and received in an annular groove in the wide duct portion 4a. This seal prevents metal from flowing directly into duct 4 from chamber 5 without first ascending through tube 6.

The slag retention chamber 5 is of cylindrical configuration, but has a dropped bottom portion to define a flow-reversing chamber 12. A feed or charge duct 8 ends in the higher bottom portion of chamber 5, in a level above the bottom of tube 6. This upper end of duct 8 is excentrically located to tube 6, but the inlet portion 9 of duct 8 is centrally disposed in the outer bottom of body 1. One can also say that feed duct 8 terminates in retention chamber 5, diametrically opposed to reversal chamber 12.

In operation, body 1 as mounted on a cardboard tube is dipped into molten steel which flows through duct 8 into chamber 5. Any slag particles inducted in the steel have the tendency to gather in the upper semitoroidal portion of slag chamber 5. The inflow of steel is a rapid one; a near jet emerges from duct 8. This jet will be converted into a clockwise eddy to reach the bottom of tube 6 via reversing chamber 2, gradually filling the same, including extension 3 for the formation of a lamella.

Any solidification of the steel in tube 6 is avoided as fresh and hot steel surrounds the tube. This heat exchange suffices to maintain the steel in tube 6 in the liquidous state. This feature is particularly important in those cases in which the state of the steel is near the liquidous line. Thus, the steel could readily solidify prematurely inside of body 1. The liquid steel around tube 6 prevents solidification of the steel rising in tube 6.

After the sample device has been withdrawn, the steel solidifies inside ceramic body 1 which is destroyed. The solidified steel is of a disk-shaped configuration on account of the contour of the mold chamber, and a pin is attached to that disk, which pin has filled tube 6 and duct 4. The content of chamber 5 is likewise solidified and hangs on that pin. The pin is usually removed for use in gas analysis. It is significant, however, that a portion of the duct filling the mold, namely duct 4, is inside the ceramic body. This permits retention of this pin when the solidified content of chamber 5 including tube 6 is removed. Spacing A between chambers 2 and 5 (length of duct 4) permits the clean separation of the pin from the content of chambers 4 and 5. It should be noted, however, that the lamella formed in chamber portion 3 permits alternative gas analysis so that the pin can be removed entirely. Please note that in either case a space is needed to permit insertion of a cutting tool between the solidified sample in mold 2 and the solidified content of chamber 5 in order to cut the pin filling duct 4. To this end, the lower portion of chamber 2 is well spaced from the uppermost portion of chamber 5.

Figure 2:
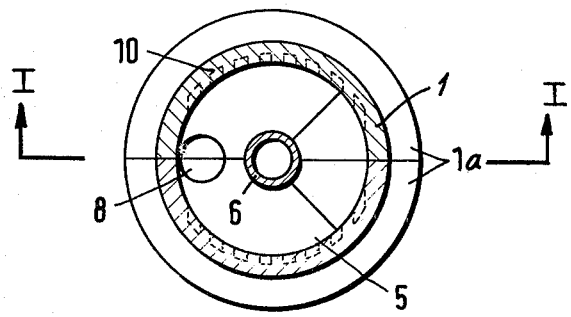
FIG. 2 is a section view taken along line II—II in FIG. 1 and showing also the section plane, I—I, for FIG. 1.

In the instance of sampling a blowing converter, it is particularly critical to obtain a slag-free sample. To this end, many small indentations 10 are provided in the wall of chamber 5. These indentations or recesses establish an overall profiled, i.e., uneven, surface for the slag retention chamber. FIG. 2 reveals in particular that these indentations 10 are not radially oriented to the center axis of chamber 5; but they are oriented in parallel, e.g., at right angles to the plane of FIG. 1. Since body 1 is manufactured in halves, these indentations are stamped into the concave, semicylindrical surfaces of both parts, each of which will become half of the wall of chamber 5. A single, rather simple, stamping tool can be used for this purpose.

It was found that little bosses rather than indents can be used for the same purpose. Moreover, it will be appreciated that the above-identified application and patent proposes the use of a sieve between slag retention chamber and mold cavity. Reference numeral 11 points to the location as being well suited for placement of such a sieve, having a pie-shaped configuration in this instance. The sieve would separate the entrance and flow-reversing chamber 12 (as to tube 6) from the major part of slag retention chamber 5.

The invention is not limited to the embodiments described above, but all changes and modifications thereof not constituting departures from the spirit and scope of the invention are intended to be included.

I claim:

1. Apparatus for sampling molten metal, e.g., steel, and including a body which contains a plurality of chambers, comprising:
    an upper, mold-defining chamber in the body for a sample;
    a lower slag retention chamber disposed underneath the mold-defining chamber;
    a duct in the body, ending upwardly in a bottom of the mold-defining chamber;
    an upright refractory tube, communicating with the duct at its lower end and traversing the slag retention chamber, the tube having a lower end disposed in a lower portion of the slag retention chamber, the tube being held by the body at least at an upper portion of the slag retention chamber;
    an eccentrically disposed, flow-reversing chamber as part of the slag retention chamber and extending under, and at a lower level of, the lower end of the tube; and
    a feed duct leading from an outside surface to the slag retention chamber.

2. An apparatus as in claim 1, wherein the slag retention chamber is of essentially cylindrical configuration, said tube traversing the retention chamber concentrically.

3. An apparatus as in claim 1, and including a sealing ring between the upper portion of the tube and the portion of body in which the upper portion of the tube is inserted.

4. An apparatus as in claim 3, said tube being also held in its lower portion.

5. An apparatus as in claim 1, said retention chamber having an uneven wall surface.

6. An apparatus for sampling molten metal, wherein a ceramic body is provided with a mold chamber for a sample, the chamber being disposed in the top part of the body, the improvement comprising:
    a cylindrical slag retention chamber disposed underneath the mold chamber;
    duct means including a refractory tube traversing the retention chamber concentrically and terminating in the mold chamber;
    an eccentric feed duct leading into the retention chamber; and
    a likewise eccentrically disposed depressed bottom of the slag retention chamber, serving as a flow-reversing chamber, the feed duct terminating in the slag retention chamber offset from and in a level above said depressed bottom as well as above a lower end of said refractory tube.

* * * * *